US012672777B2

(12) United States Patent
Yan et al.

(10) Patent No.: US 12,672,777 B2
(45) Date of Patent: Jul. 7, 2026

(54) HIGHLY RELIABLE IMPLANTABLE DEVICE OF IMPLANTABLE BIOLOGICAL SENSOR

(71) Applicant: Shenzhen Refresh Biosensing Technology Co., Ltd., Shenzhen (CN)

(72) Inventors: Dan Yan, Shenzhen (CN); Sheng Fu, Shenzhen (CN); Guanhua Li, Shenzhen (CN); Zhe Zhang, Shenzhen (CN); Qinglong Dong, Shenzhen (CN)

(73) Assignee: Shenzhen Refresh Biosensing Technology Co., Ltd., Shenzhen (CN)

( * ) Notice: Subject to any disclaimer, the term of this patent is extended or adjusted under 35 U.S.C. 154(b) by 554 days.

(21) Appl. No.: 18/143,589

(22) Filed: May 4, 2023

(65) Prior Publication Data

US 2024/0138678 A1    May 2, 2024

(30) Foreign Application Priority Data

Oct. 31, 2022    (CN) .......................... 202211345978.2

(51) Int. Cl.
*A61B 5/00*        (2006.01)
*A61B 5/145*       (2006.01)

(52) U.S. Cl.
CPC ............ *A61B 5/0031* (2013.01); *A61B 5/145* (2013.01); *A61B 5/68* (2013.01); *A61B 2562/16* (2013.01);
(Continued)

(58) Field of Classification Search
CPC ......... A61B 5/0031; A61B 5/145; A61B 5/68; A61B 2562/16; A61B 2562/18;
(Continued)

(56) References Cited

U.S. PATENT DOCUMENTS

2005/0101912 A1*  5/2005  Faust ................... A61M 5/158
                                                          604/117
2009/0124979 A1*  5/2009  Raymond ......... A61M 5/14244
                                                          604/195
(Continued)

FOREIGN PATENT DOCUMENTS

CN      114795193 A  *  7/2022  ......... A61B 5/14503
CN      114795194 A  *  7/2022  ......... A61B 5/14503

OTHER PUBLICATIONS

Zhang et al., Chinese Patent Document CN 114795194A—citing to translation from Espacenet.com (Year: 2022).*
(Continued)

*Primary Examiner* — Jennifer Robertson
*Assistant Examiner* — Jonathan Drew Moroneso

(57)                ABSTRACT

The present invention discloses a highly reliable implantable device of an implantable biological sensor. Before use, the fixed seat cannot move relative to the slidable seat, achieving reliable transportation. In use, the lower end face of the slidable seat is pressed against the skin; the lower end face of the first snap-fit protrusion squeezes the upper end face of the vertical snap-fit plate; the first snap-fit protrusion is gradually away from the support of the vertical snap-fit plate, whereby the inside vertical face of the vertical snap-fit plate pushes the first snap-fit protrusion inward, and the fixed seat moves downward relative to the slidable seat, achieving good controllability.

9 Claims, 12 Drawing Sheets

(52) U.S. Cl.
CPC .... *A61B 2562/18* (2013.01); *A61M 2230/201*
(2013.01)

(58) Field of Classification Search
CPC . A61B 5/14503; A61B 5/14532; A61B 5/686;
A61B 5/6847; A61M 2230/201
See application file for complete search history.

(56) References Cited

U.S. PATENT DOCUMENTS

| | | | | |
|---|---|---|---|---|
| 2011/0060287 A1* | 3/2011 | Ambruzs | .............. | A61M 5/158 604/164.12 |
| 2013/0150691 A1* | 6/2013 | Pace | ................ | A61B 5/150022 600/347 |
| 2017/0188912 A1* | 7/2017 | Halac | ................. | A61B 5/14503 |
| 2018/0235520 A1* | 8/2018 | Rao | ...................... | A61B 5/6849 |
| 2022/0225899 A1* | 7/2022 | Peterson | ............ | A61B 5/14503 |

OTHER PUBLICATIONS

Zhang et al., Chinese Patent Document Cn 114795193A—citing to
translation from Espacenet.com (Year: 2022).*

* cited by examiner

HIGHLY RELIABLE IMPLANTABLE DEVICE OF IMPLANTABLE BIOLOGICAL SENSOR

CROSS REFERENCE TO RELATED APPLICATIONS

The present application claims the benefit of Chinese Patent Application No. 202211345978.2 filed on Oct. 31, 2022, the contents of which are incorporated herein by reference in their entirety.

TECHNICAL FIELD

The invention relates to the technical field of biological sensor, in particular to a highly reliable implantable device of an implantable biological sensor.

BACKGROUND ART

For people with diabetes, the traditional fingertip glucometer has such shortcomings as being invasive, providing limited information, and being unable to reflect blood glucose fluctuations and provide early warning, so it cannot meet the needs of some people, especially type 1 diabetes patients who need real-time transmission of blood glucose fluctuations and type 2 diabetes patients who need intensive insulin treatment.

To meet the need for continuous blood glucose monitoring, it is necessary to use the highly reliable implantable device and internal components of an implantable biosensor to implant the sensor into the subcutaneous tissue of the human body to measure the blood glucose concentration between tissue fluids, which is a means of continuous monitoring that can be employed in reality. The single service life of the implantable biosensor is one to two weeks, which greatly reduces the pain caused by continuous fingertip blood sampling and venous blood sampling. At present, such implantable devices on the market have problems such as complex user operation, long implantation process, and easiness to trigger the push device by mistake, which reduces the user compliance (patient compliance/treatment compliance refers to the extent to which a patient follows medical advice and instructions for their treatment, and is also called patient "cooperation"; otherwise, it is called non-compliance) and degrades the user experience.

The small size of the transmitter (the device including implantable sensing electrode and used to transmit the monitored biological signal) helps to improve the wearing experience. The implantable sensing electrode of the transmitter needs to be implanted under the human body skin. During the assembly, transportation and implantation processes, etc., the fixed seat of the fixed transmitter and the slidable seat need to remain fixed relative to each other at the appropriate time, and undergo relative sliding under certain conditions, in order to achieve the implantation of the implantable sensing electrode and the retraction of the implantable needle. In the prior art, the fit between the fixed seat of the fixed transmitter and the slidable seat is not very reasonable.

SUMMARY OF THE INVENTION

In view of the above, the present invention provides a highly reliable implantable device of an implantable biological sensor. During the assembly, transportation and implantation processes, the relevant structures of the fixed seat and the slidable seat can fit well, and are highly reliable when the implantable sensing electrode is implanted into the skin of the human body.

A highly reliable implantable device of an implantable biological transmitter comprises a slidable seat and a fixed seat. The lower circumference of the fixed seat is used to snap-fit with an implantable biological transmitter. A cantilever hook beam and a support frame extend upwards from an isolating wall of the fixed seat. There are two or more cantilever hook beams. The partition plate of the slidable seat is provided with two or more first grooves. The partition plate of the slidable seat is provided with a snap-fit frame and a fixed seat extension slot. There are two or more first grooves.

The support frame extends out from the snap-fit frame, and is slidable along the snap-fit frame.

A vertical snap-fit plate extends upwards from the partition plate on the outer side the first groove, and the first groove is located on the side of the fixed seat extension slot.

A first snap-fit protrusion extends outward from the upper end of the cantilever hook beam.

A gap is provided between the inner side of the cantilever hook beam and the support frame, and a gap is provided between the outer side of the cantilever hook beam and the vertical portion of the vertical snap-fit plate.

After leaving the factory and before use: the upper wall face of the isolating wall abuts against the bottom wall face of the partition plate, and the fixed seat cannot move upward relative to the slidable seat; the cantilever hook beam extends out from the first groove, part of the first snap-fit protrusion is snap-fit at the upper end of the vertical snap-fit plate, and the fixed seat cannot move downward relative to the slidable seat.

In use, the lower end face of the slidable seat is pressed against the skin. The fixed seat is pushed downward. The cantilever hook beam tends to move downward with the fixed seat. The lower end face of the first snap-fit protrusion starts to squeeze the upper end face of the vertical snap-fit plate. Under the reaction force of the upper end face of the vertical snap-fit plate, the upper end of the cantilever hook beam is deformed inward and upward relative to its bottom, and the first snap-fit protrusion is gradually away from the support of the upper end face of the vertical snap-fit plate. A downward thrust is further applied to the fixed seat. The inside vertical face of the vertical snap-fit plate pushes the first snap-fit protrusion inward. The fixed seat moves downward relative to the slidable seat.

Preferably, the first snap-fit protrusion is partially snap-fit at the upper end of the vertical snap-fit plate; the lower straight plane of the first snap-fit protrusion is pressed on the upper straight plane of the vertical snap-fit plate; and 30%-90% of the extension length of the first snap-fit protrusion is snap-fit at the upper end of the vertical snap-fit plate.

The first snap-fit protrusion snap-fit at the upper end of the vertical snap-fit plate relates to the issue of how much is pushed. We define it as the amount of interference. In the case where it can be pushed open, a small amount of interference requires a small trigger force, and a big amount of interference requires a big trigger force. An appropriate amount of interference is controlled, and a structure which meets the required trigger force value can be designed. If the amount of interference is too large, the vertical snap-fit plate cannot push open the cantilever hook beam. If the amount of interference is too small, under mechanical disturbance or vibration, the vertical snap-fit plate can break the restraint of the cantilever hook beam, and it cannot perform the function of locking in this state.

Preferably, the support frame is configured to be slidable along the snap-fit frame.

The outer side of the support frame is provided with a first vertical snap-fit strip, and the inner side of the snap-fit frame is provided with a first vertical snap-fit slot; the first vertical snap-fit strip is slidable along the first vertical snap-fit slot.

The snap-fit frame is divided into four portions, respectively located on the circumference of the fixed seat extension slot. The corresponding support frame is divided into four portions. A first vertical snap-fit slot is provided on the inner side of the snap-fit frame of each portion. A first vertical snap-fit strip is provided on the outer side of the support frame of each portion. Each first vertical snap-fit strip fits into a first vertical snap-fit slot correspondingly.

Preferably, it further comprises a needle drive and a compression spring.

An inner jaw is provided on the inner side the needle drive for snap-fit with the needle aid, and a snap-fit column in the spring extends upwards from the isolating wall on the inner side the support frame.

The support frame further comprises a cantilever pressure contact beam, which is provided on the upper end with a pressure contact facing inward.

The upper portion of the snap-fit frame is provided with a section of pressure contact plate.

After leaving the factory and before use: the lower end of the compression spring abuts against the upper wall face of the isolating wall. The upper end of the compression spring abuts against the inner bottom face of the needle drive. The lower portion of the compression spring is sleeved outside the snap-fit column in the spring. The upper portion of the compression spring is sleeved outside the inner jaw. The pressure contact is pressed against the bevel on the circumference of the needle drive. The pressure-contact face of the pressure contact is also a bevel. Pressed by the pressure contact plate on the outside, the cantilever pressure contact beam cannot be deformed outward.

In use, after the fixed seat moves down for a distance relative to the slidable seat, the needle aid completes the implantation action. The cantilever pressure contact beam is released from the pressure contact of the pressure contact plate. Under the effect of the elastic potential energy of the compression spring, the needle drive pushes open the pressure contact. The inner jaw of the needle drive drives the needle aid to move upward to complete the needle withdrawal.

The snap-fit frame is divided into four portions. There are four pressure contact plates. A pressure contact plate is provided between each pair of snap-fit frames. There are four cantilever pressure contact beams. Each pressure contact plate corresponds to a cantilever pressure contact beam.

The snap-fit column inside the spring is distributed in an arc shape. There are four or more snap-fit columns inside the spring. The snap-fit columns inside the spring are distributed in a circumferential array to be stably supported on the inner side the compression spring.

Preferably, it further comprises a main housing, which is provided with a second vertical snap-fit slot and a snap-fit plate. The snap-fit plate is provided with a snap-fit groove. A snap-fit block is provided on the outer side the support frame. The upper portion of the first vertical snap-fit strip is snapped into the second vertical snap-fit slot. The snap-fit block is fitted in the snap-fit groove. The main housing is located on the outer side the slidable seat and the fixed seat.

It further comprises an upper cover. The upper cover fits on the outer side of the main housing through a snap-fit interface to facilitate the assembly of the overall structure.

Preferably, it further comprises a main device protective jacket. The lower circumference of the fixed seat is for snap-fit with the implantable biological transmitter. The main device protective jacket snap-fits with the lower portion of the main housing. The slidable seat and the fixed seat are located in the space formed by the main device protective jacket and the main housing.

The implantable biological transmitter includes a transmitter main body and an implantable sensing electrode. The transmitter main body and the implantable sensing electrode have been assembled. Alternatively, the implantable biological transmitter does not include the implantable sensing electrode. Instead, the assembly of the main body of the implantable biological transmitter and the implantable sensing electrode is completed in a preceding step before implantation.

Preferably, it further comprises a needle aid, which comprises an implantable needle and a needle seat. The needle seat is provided at the upper end with a snap-fit groove for snap-fit with the inner jaw.

When it leaves the factory, the inner jaw snap-fits with the snap-fit groove of the needle seat. Alternatively, snap-fit between the inner jaw and the snap-fit groove of the needle seat is achieved through the first step action after it leaves the factory and before implantation.

Preferably, it further comprises an anti-trigger sleeve, which is snap-fit between the main housing and the main device protective jacket.

The main device protective jacket is provided at the bottom with an assembly snap-fit seat. The assembly snap-fit seat is used for snap-fit with the sensing electrode assembly. The sensing electrode assembly comprises an electrode protective jacket, a needle aid and an implantable sensing electrode.

After leaving the factory and before use: the sensing electrode assembly and the main body of the implantable biological transmitter are configured separately. The implantable biological transmitter fit at the lower circumference of the fixed seat only comprises the main body and does not comprise the implantable sensing electrode.

In the first stage before implantation, the anti-trigger sleeve is removed first, so that the main housing moves relative to the main device protective jacket. The main housing drives the main body of the implantable biological transmitter close to the sensing electrode assembly through the fixed seat, completing the fit between the main body of the implantable biological transmitter and the implantable sensing electrode.

The transmitter is in a working or silent state when it is placed inside the implantable assembly. However, no matter which way, the transmitter and the sensor assembly have already been electrically connected. Due to the small size of the transmitter, the size of the battery is limited, leading to a small battery capacity. The hardware must have an extremely low power consumption to meet the requirements for the shelf life of the product (shelf life is the guarantee of and commitment to the quality and efficacy of a commodity in the circulation period).

The beneficial effects of the invention are as follows: the present invention discloses a highly reliable implantable device of an implantable biological sensor. After leaving the factory and before use: the upper wall face of the isolating wall abuts against the bottom wall face of the partition plate, and the fixed seat cannot move upward relative to the slidable seat; the cantilever hook beam extends out from the first groove, part of the first snap-fit protrusion is snap-fit at the upper end of the vertical snap-fit plate, and the fixed seat cannot move downward relative to the slidable seat, ensuring the reliability during transportation. In use, the lower end face of the slidable seat is pressed against the skin; the fixed seat is pushed downward; the cantilever hook beam tends to move downward with the fixed seat; the lower end face of the first snap-fit protrusion starts to squeeze the upper end face of the vertical snap-fit plate; under the reaction force of the upper end face of the vertical snap-fit plate, the upper end of the cantilever hook beam is deformed inward and upward relative to its bottom, and the first snap-fit protrusion is gradually away from the support of the upper end face of the vertical snap-fit plate; a downward thrust is further applied to the fixed seat; the inside vertical face of the vertical snap-fit plate pushes the first snap-fit protrusion inward; and the fixed seat moves downward relative to the slidable seat, achieving good controllability and high reliability.

BRIEF DESCRIPTION OF THE DRAWINGS

The following is a further description of a highly reliable implantable device of an implantable biological sensor of the invention in combination with the drawings.

6

Figure 1:
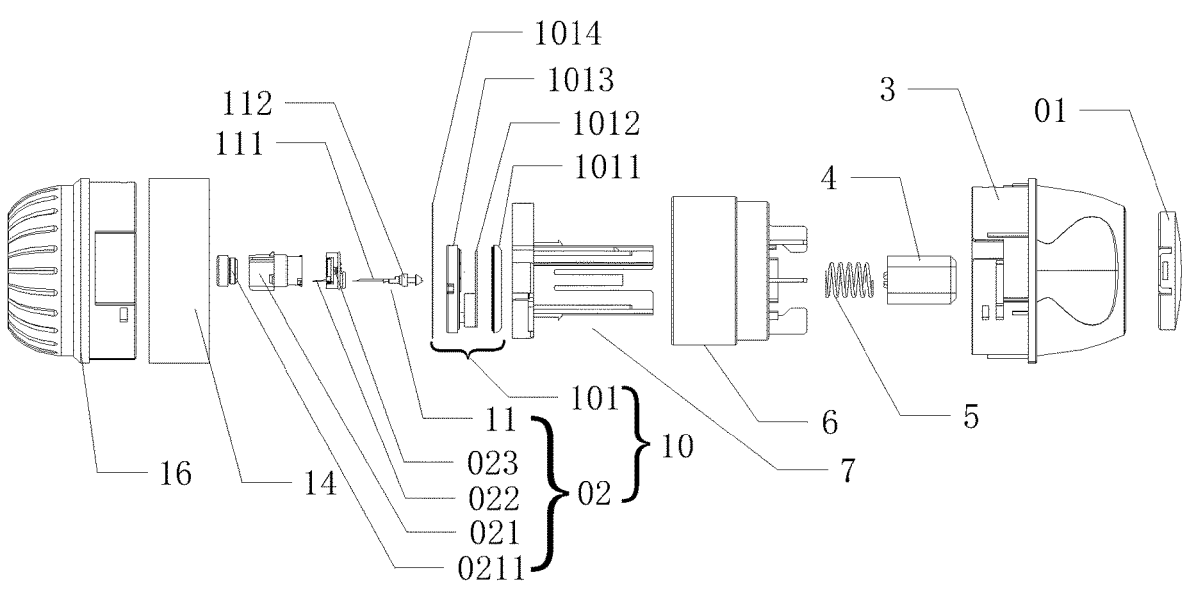
FIG. 1 is an exploded schematic structural view of a perspective of a highly reliable implantable device of an implantable biological sensor of the present invention.
Figure 2:
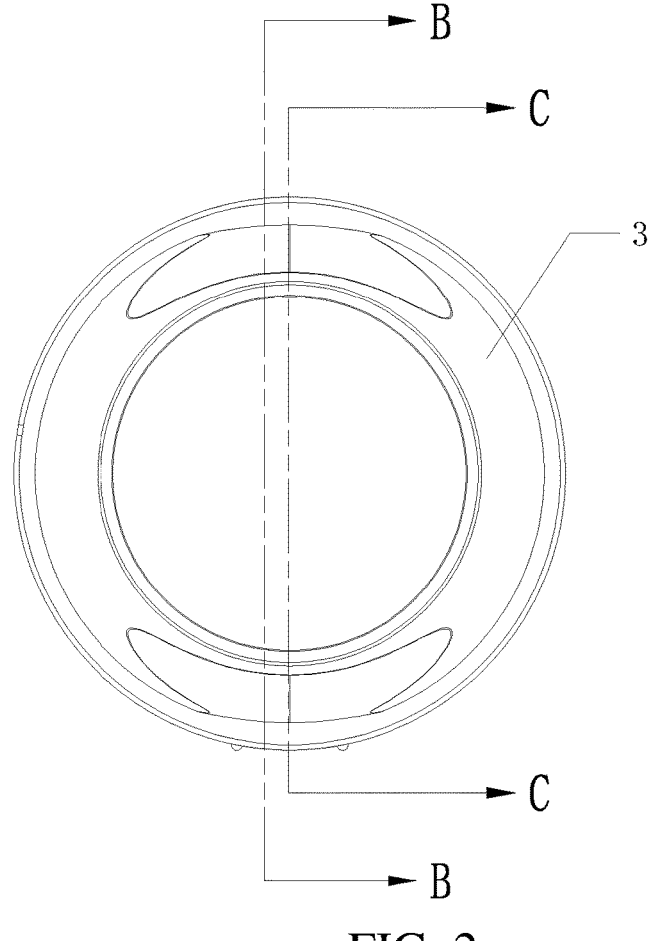
FIG. 2 is a schematic structural view of a perspective of a highly reliable implantable device of an implantable biological sensor of the present invention.
Figure 3:
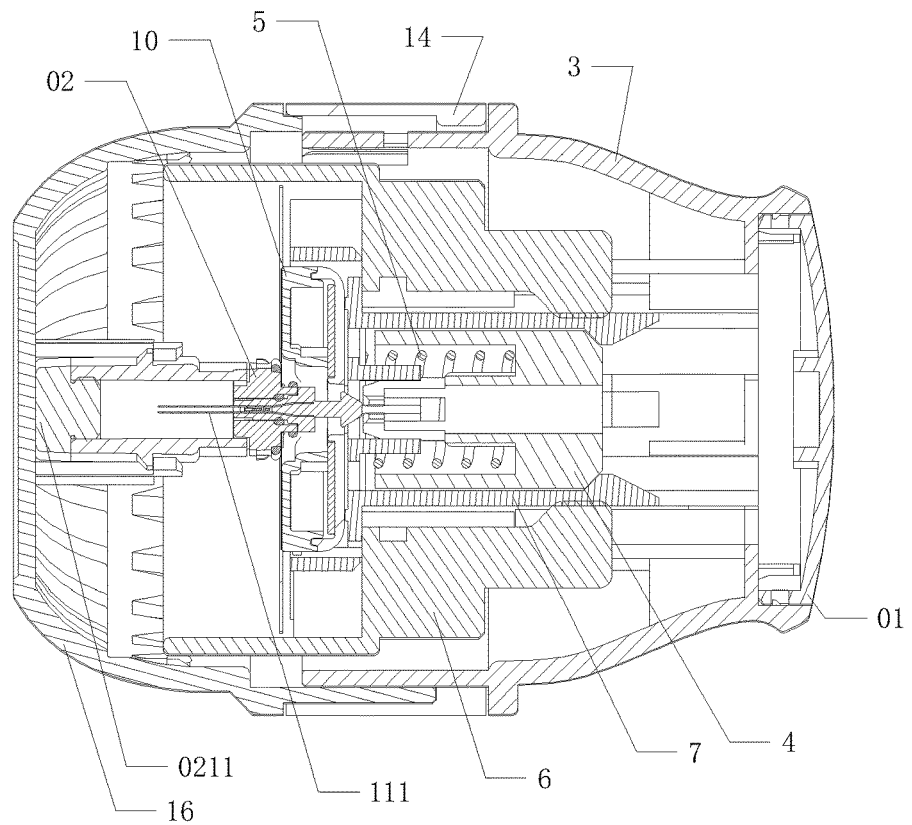
FIG. 3 is a schematic structural view of the B-B cross-section in FIG. 2 of a highly reliable implantable device of an implantable biological sensor of the present invention.
Figure 4:
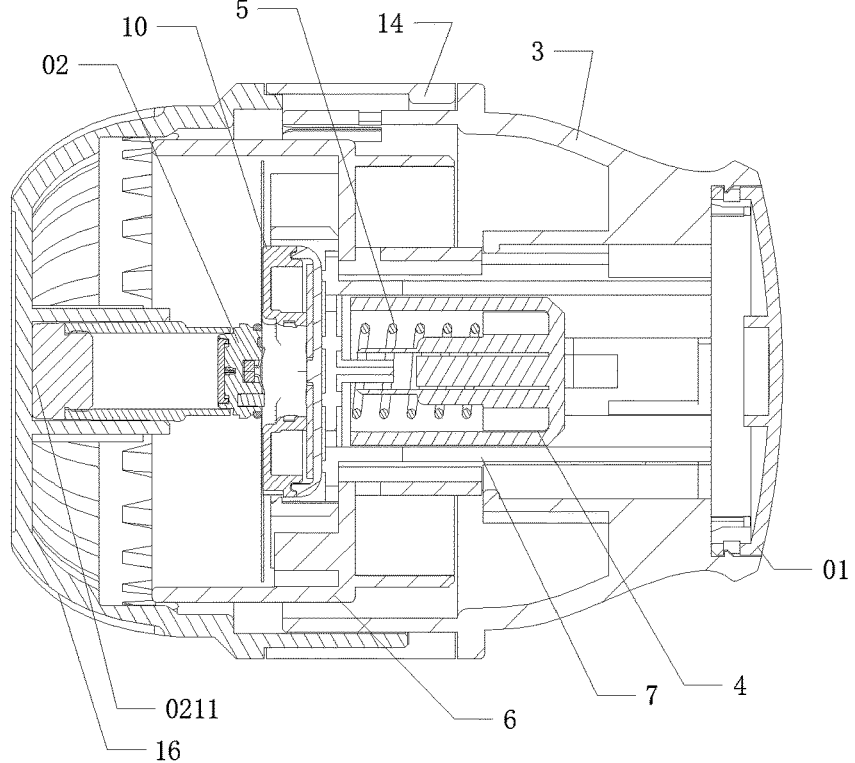
FIG. 4 is a schematic structural view of the C-C cross-section in FIG. 2 of a highly reliable implantable device of an implantable biological sensor of the present invention.
Figure 5:
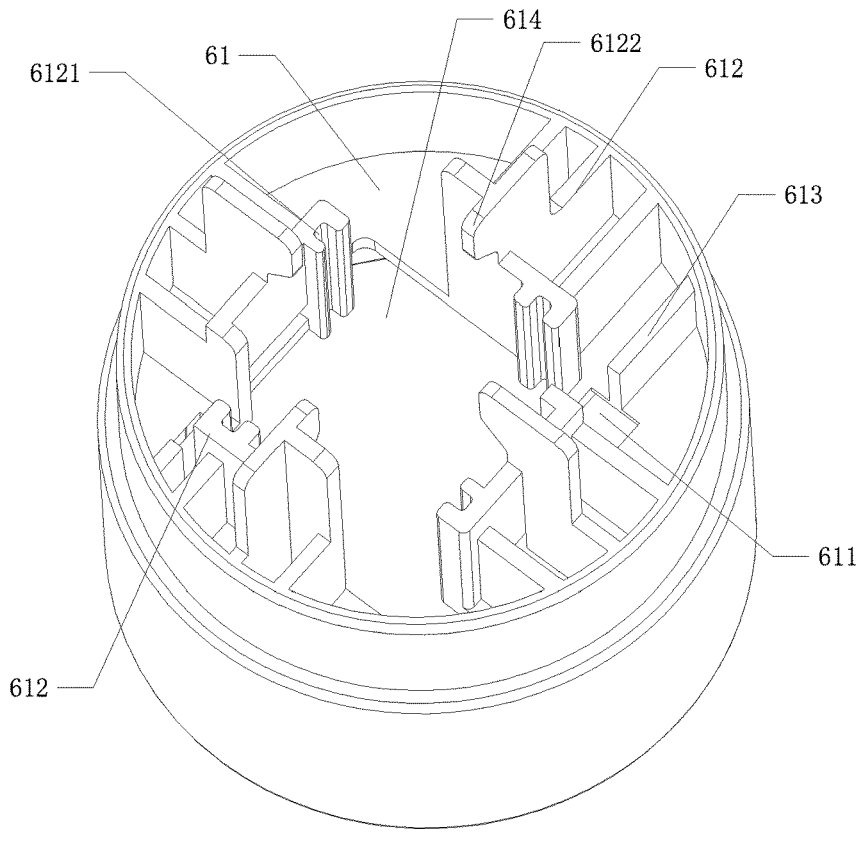
FIG. 5 is a schematic structural view of a perspective of a slidable seat of a highly reliable implantable device of an implantable biological sensor of the present invention.
Figure 6:
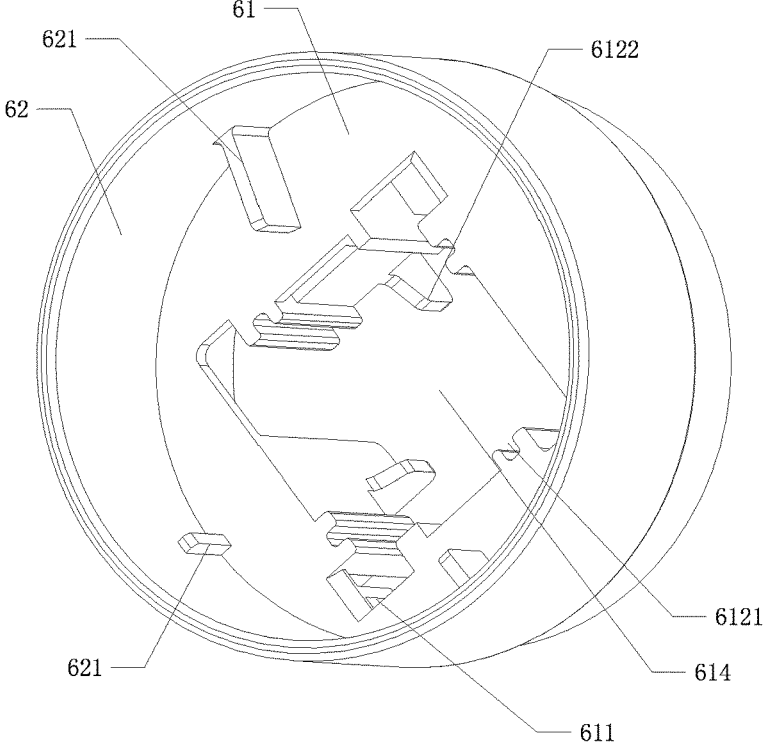
FIG. 6 is a schematic structural view of another perspective of a slidable seat of a highly reliable implantable device of an implantable biological sensor of the present invention.
Figure 7:
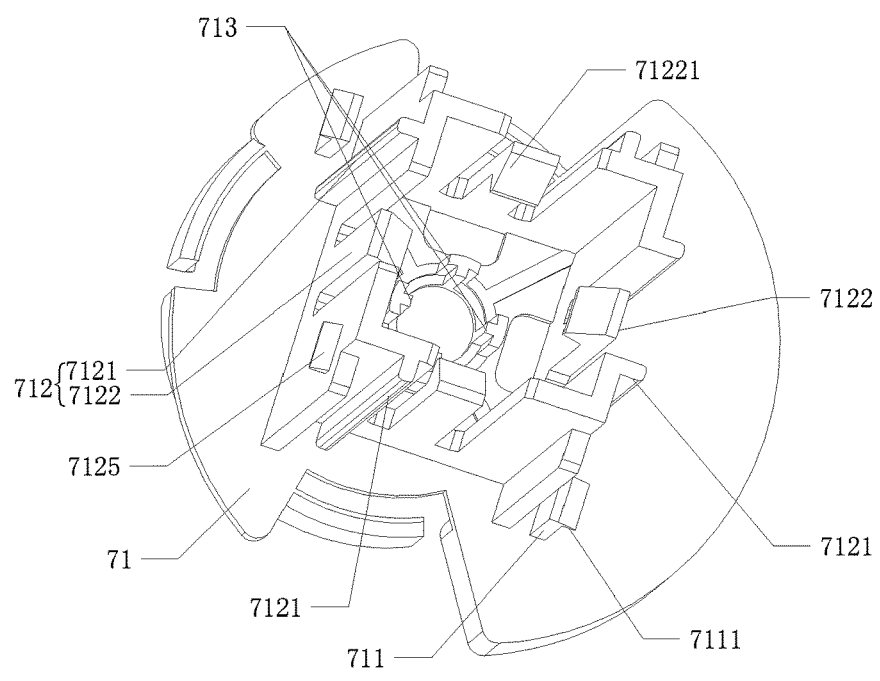
FIG. 7 is a schematic structural view of a perspective of a fixed seat of a highly reliable implantable device of an implantable biological sensor of the present invention.
Figure 8:
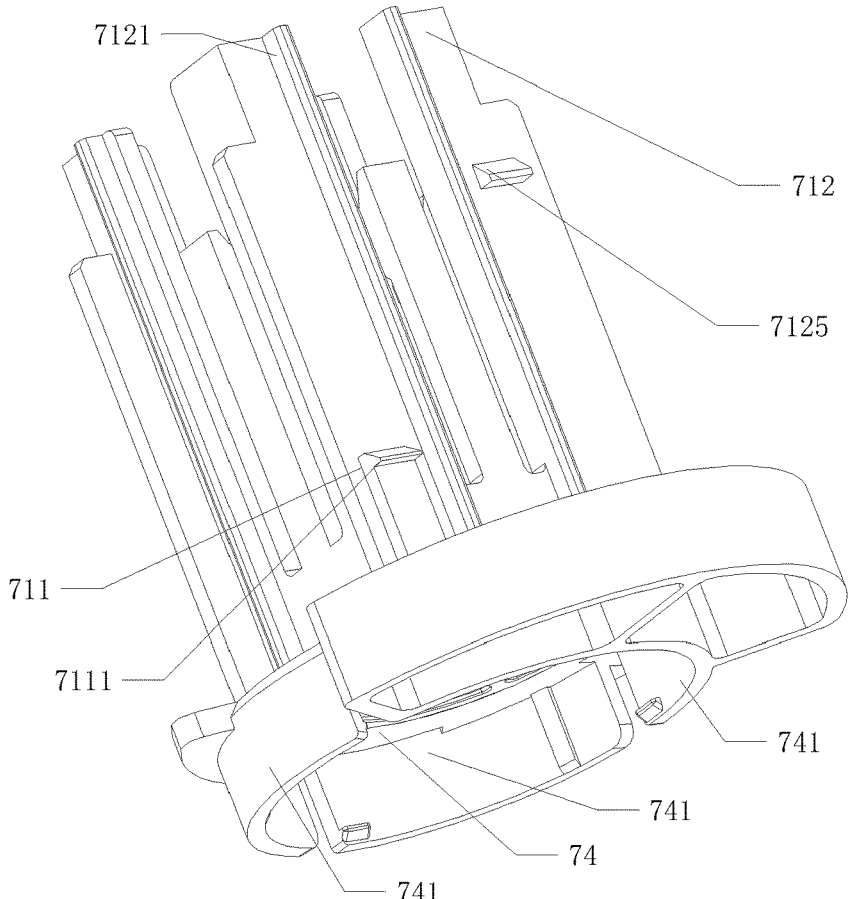
FIG. 8 is a schematic structural view of another perspective of a fixed seat of a highly reliable implantable device of an implantable biological sensor of the present invention.
Figure 9:
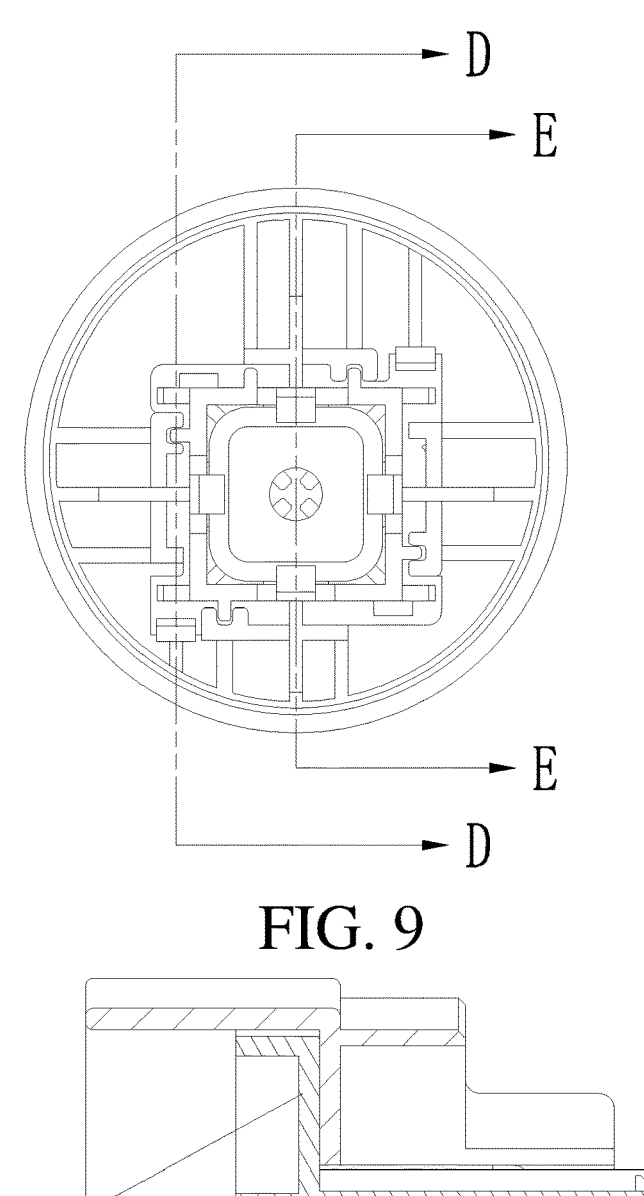
FIG. 9 is a schematic structural view of a perspective of the fit between a fixed seat and a slidable seat of a highly reliable implantable device of an implantable biological sensor of the present invention, in the initial state after assembly.
Figure 10:
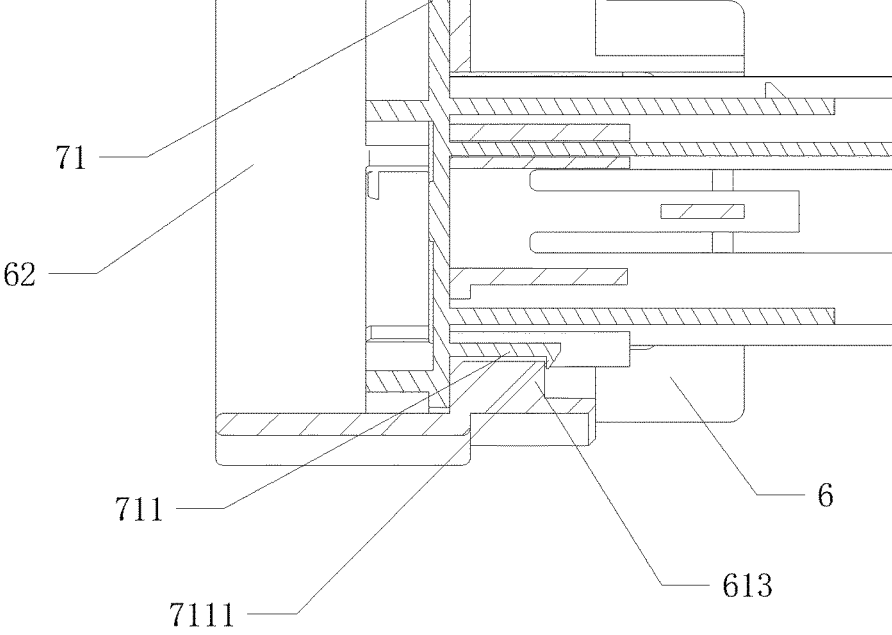
FIG. 10 is a schematic structural view of the D-D cross-section in FIG. 9 of a highly reliable implantable device of an implantable biological sensor of the present invention.
Figure 11:
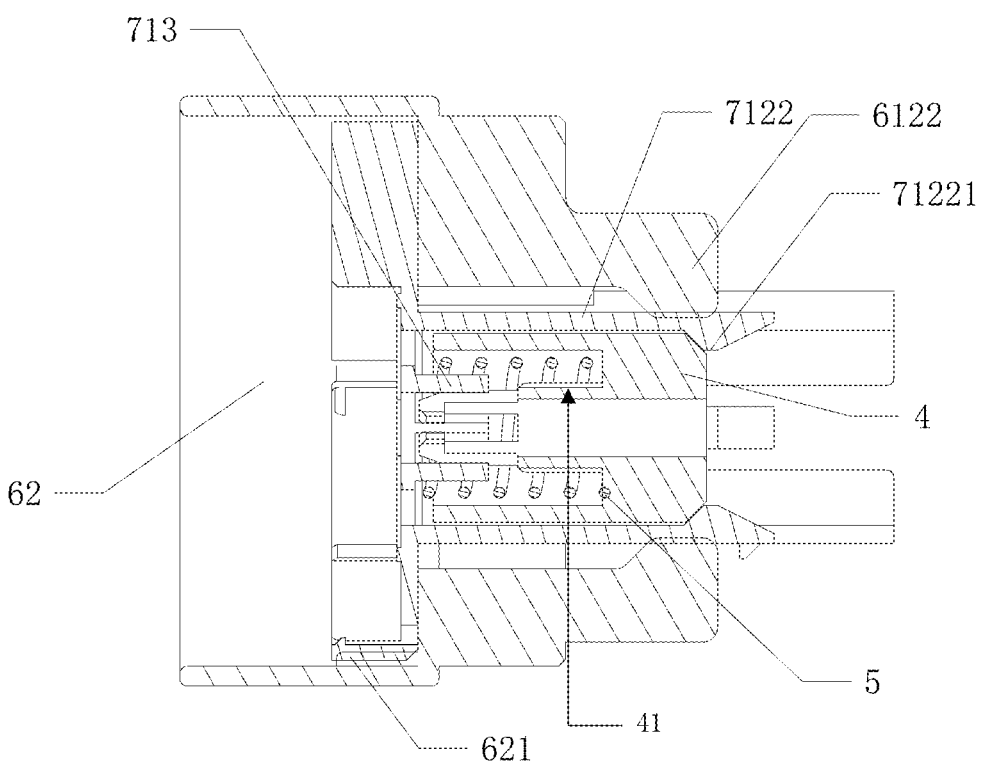
FIG. 11 is a schematic structural view of the E-E cross-section in FIG. 9 of a highly reliable implantable device of an implantable biological sensor of the present invention.
Figure 12:
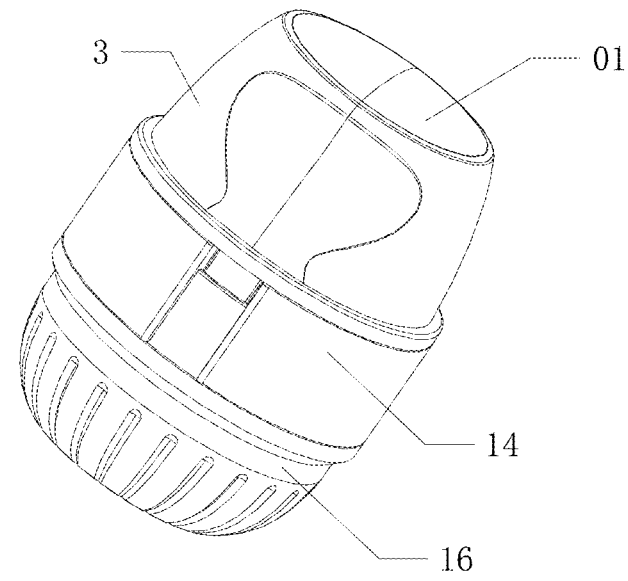
FIG. 12 is a schematic structural view of a perspective of the initial state of a highly reliable implantable device of an implantable biological sensor of the present invention.
Figure 13:
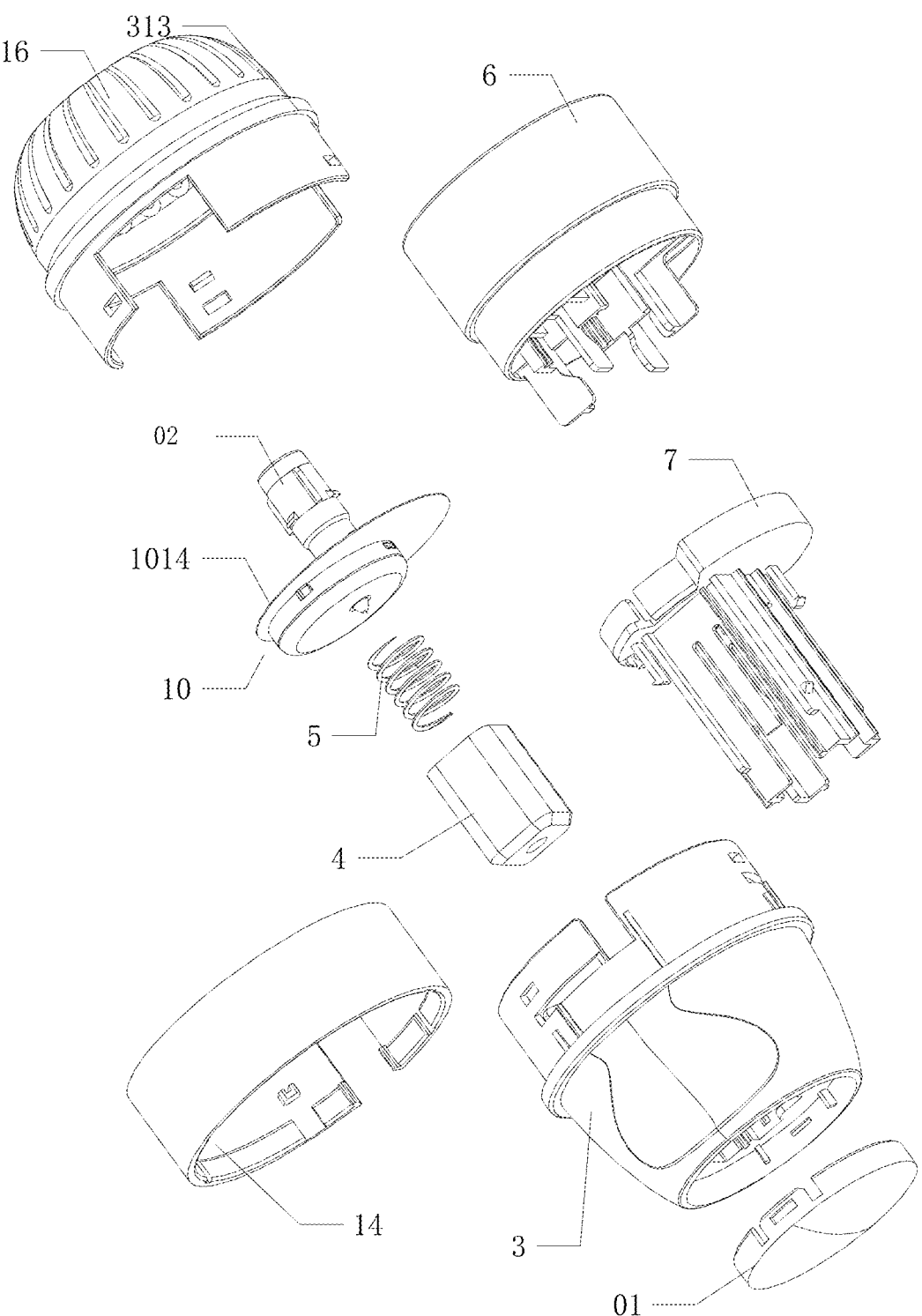
FIG. 13 is an exploded schematic structural view of the initial state of a highly reliable implantable device of an implantable biological sensor of the present invention, wherein the implantable biological transmitter and the sensing electrode assembly are not assembled.
Figure 14:
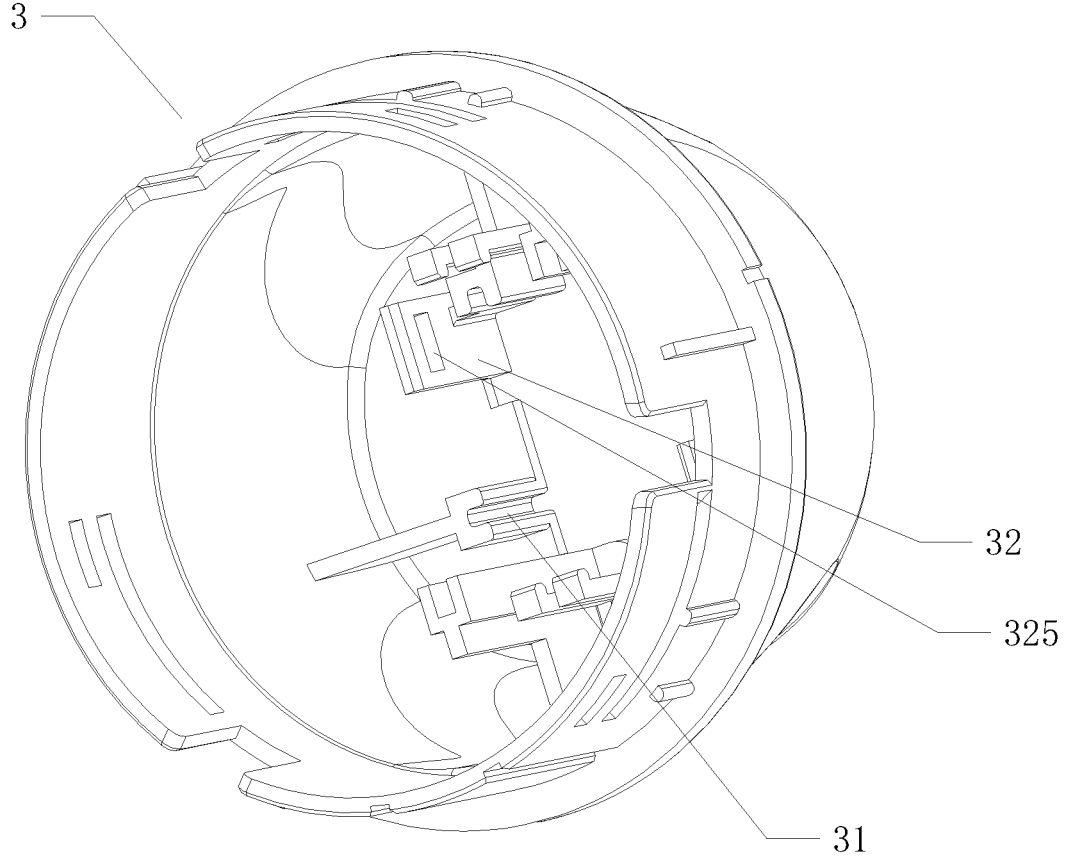

FIG. 14 is a schematic structural view of a perspective of a main housing of a highly reliable implantable device of an implantable biological sensor of the present invention.

Figure 15:
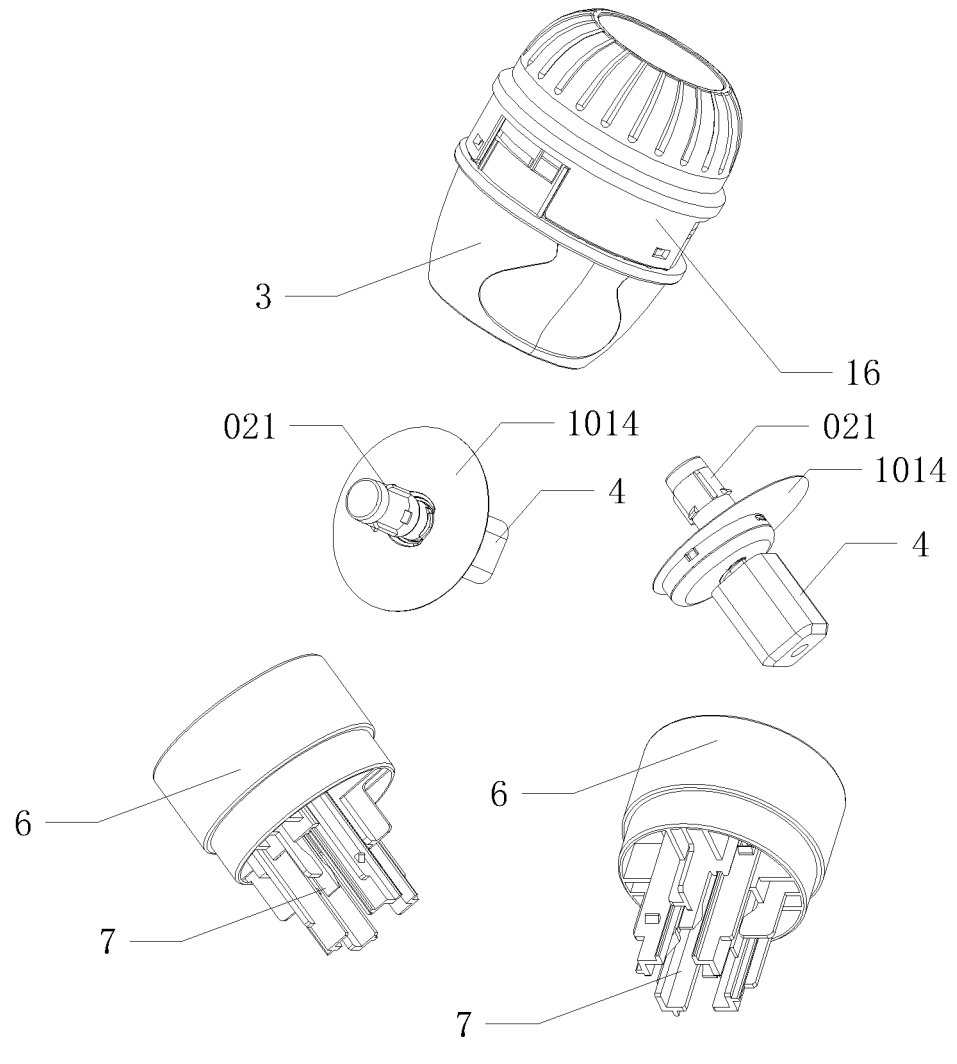

FIG. 15 is a schematic structural view of an implantable biological transmitter and a sensing electrode assembly of a highly reliable implantable device of an implantable biological sensor of the present invention after assembly, wherein views of two perspectives of the implantable biological transmitter and the sensing electrode assembly, views of two perspectives of the fit between the fixed seat and the slidable seat, and an overall outlook view of the structure are provided.

Figure 16:
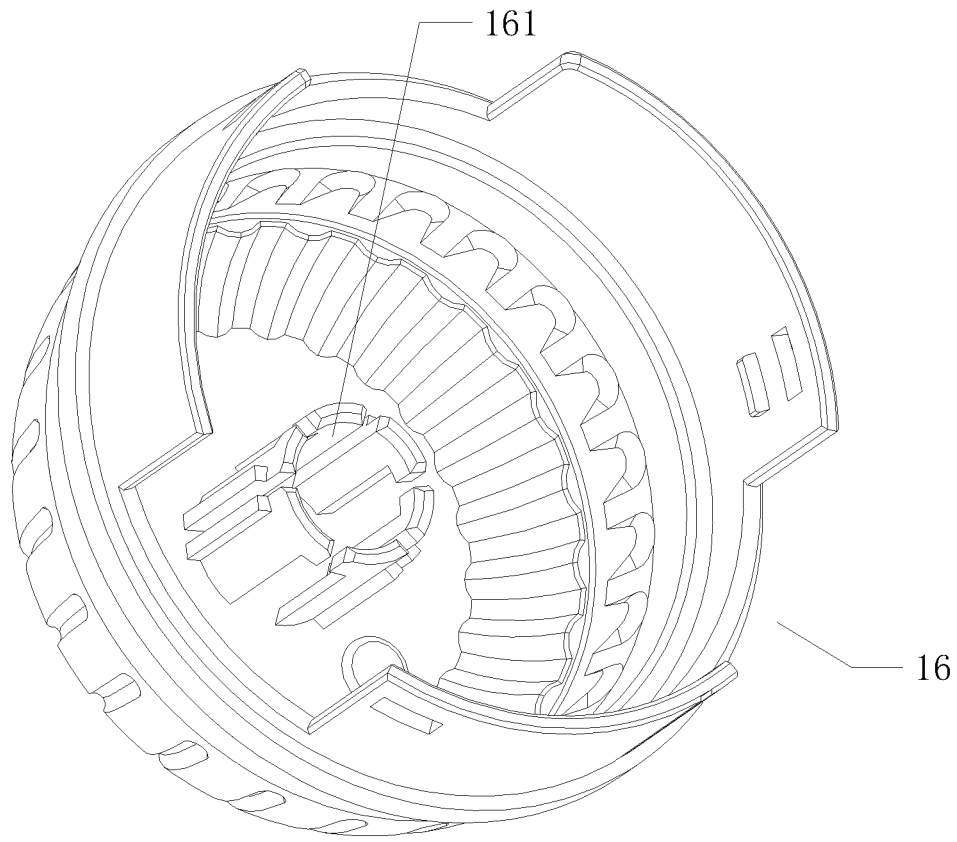

FIG. 16 is a schematic structural view of a perspective of a protective jacket of a highly reliable implantable device of an implantable biological sensor of the present invention.

Figure 17:
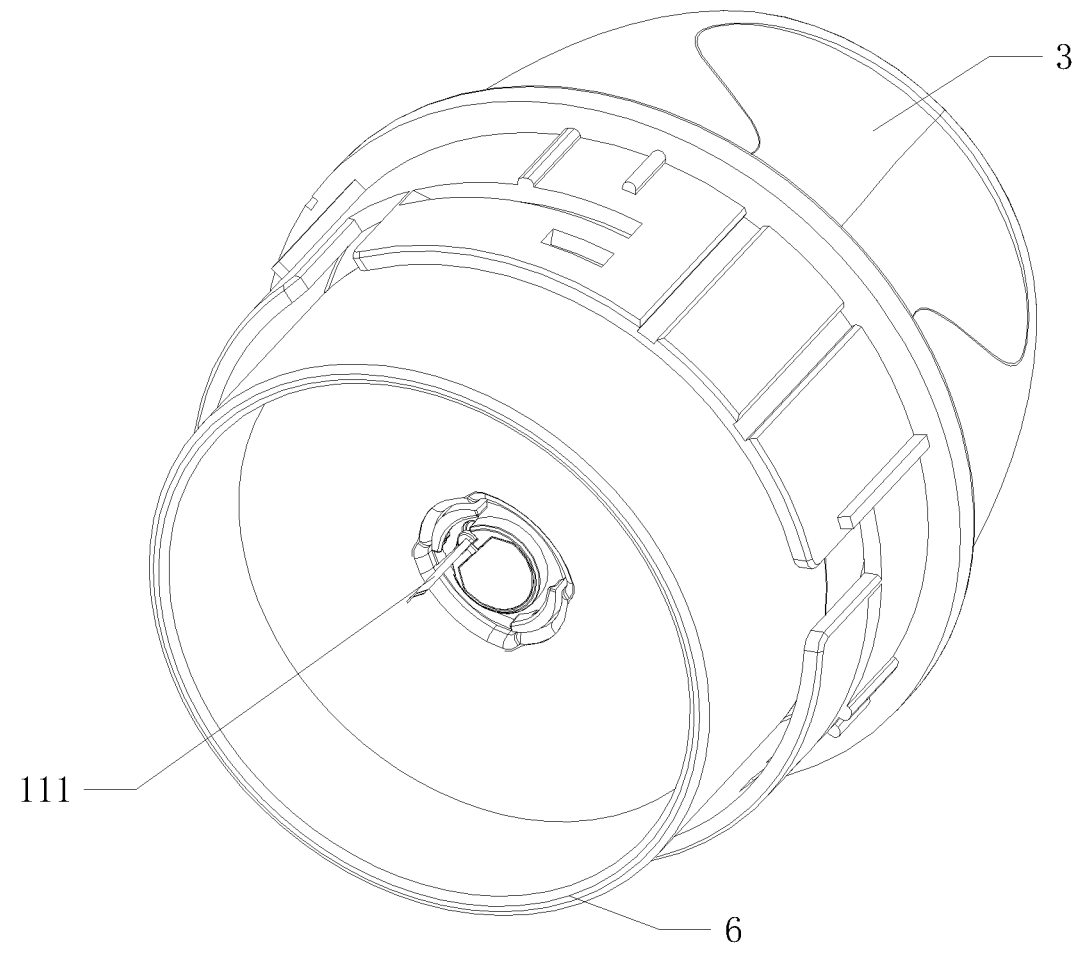

FIG. 17 is a schematic structural view of a highly reliable implantable device of an implantable biological sensor of the present invention, wherein the protective jacket can be removed before implantation of the implantable biological transmitter, and the implantable needle can be seen.

Figure 18:
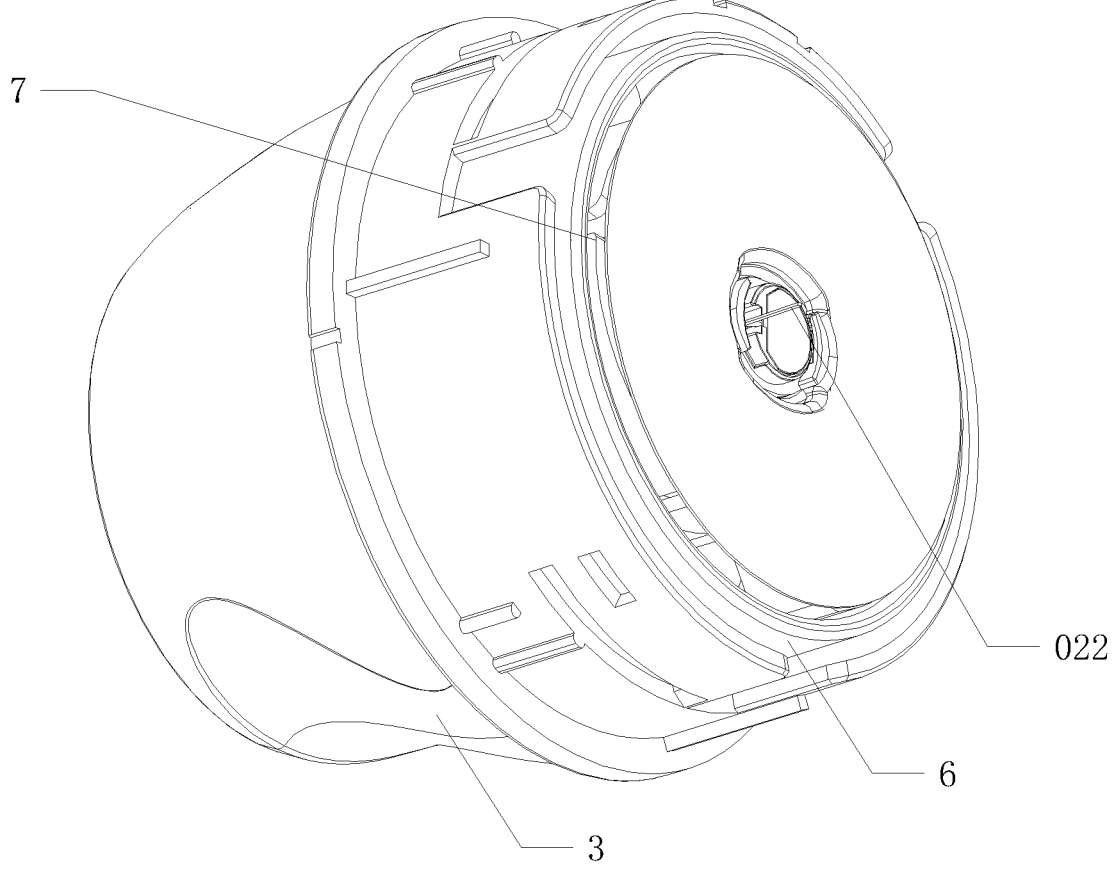

FIG. 18 is a schematic structural view of a highly reliable implantable device of an implantable biological sensor of the present invention, wherein the implantable sensing electrode can be seen after implantation of the implantable biological transmitter.

In the figures:

3—main housing; 31—second vertical snap-fit slot; 32—snap-fit plate; 325—snap-fit groove; 4—needle drive; 41—inner jaw; 5—compression spring; 6—slidable seat; 61—partition plate; 611—first groove; 612—snap-fit frame; 6121—first vertical snap-fit slot; 6122—pressure contact plate; 613—vertical snap-fit plate; 614—fixed seat extension slot; 62—fixed seat accommodating cavity; 621—snap-fit finger; 7—fixed seat; 71—isolating wall; 711—cantilever hook beam; 7111 first snap-fit protrusion; 712—support frame; 7121—first vertical snap-fit strip; 7122—cantilever pressure contact beam; 71221—pressure contact; 7125—snap-fit block; 713—snap-fit column in the spring; 74—transmitter accommodating cavity; 741—arc-shaped cantilever snap-fit beam; 10—implantable biological transmitter; 101—Main body; 1011—transmitter upper cover; 1012—transmitter PCBA; 1013—transmitter housing; 1014—double-sided adhesive; 11—needle aid; 111—implantable needle; 112—needle seat; 14—anti-trigger sleeve; 16—main device protective jacket; 161—assembly snap-fit seat; 01—upper cover; 02—sensing electrode assembly; 021—electrode protective jacket; 0211—Soft plug; 022—implantable sensing electrode; 023—electrode assembly main body.

DETAILED DESCRIPTION OF THE DRAWINGS

The following is a further description of a highly reliable implantable device of an implantable biosensor of the present invention in conjunction with FIGS. 1 to 18.

A highly reliable implantable device of an implantable biological transmitter comprises a slidable seat 6 and a fixed seat 7. The lower circumference of the fixed seat 7 is used to snap-fit with an implantable biological transmitter 10. A cantilever hook beam 711 and a support frame 712 extend upwards from an isolating wall 71 of the fixed seat 7. There are two or more cantilever hook beams 711. Two cantilever hook beams 711 are provided two opposite sides of the isolating wall 71. The partition plate 61 of the slidable seat 6 is provided with two or more first grooves 611. The partition plate 61 of the slidable seat 6 is provided with a snap-fit frame 612 and a fixed seat extension slot 614. The snap-fit frame 612 constitutes the upper portion of the fixed seat extension slot 614. The fixed seat extension slot 614 is provided in the middle position of the partition plate 61. The snap-fit frame 612 is on the circumference of the fixed seat extension slot 614. There are two or more first grooves 611. The number of the first groove 611 corresponds to the number of the cantilever hook beam 711. Each cantilever hook beam 711 extends out from one first groove 611.

The support frame 712 extends out from the snap-fit frame 612, and is slidable along the snap-fit frame 612.

A vertical snap-fit plate 613 extends upwards from the partition plate 61 on the outer side the first groove 611, and the first groove 611 is located on the side of the fixed seat extension slot 614.

A first snap-fit protrusion 7111 extends outward from the upper end of the cantilever hook beam 711.

A gap is provided between the inner side of the cantilever hook beam 711 and the support frame 712. A gap is provided between the outer side of the cantilever hook beam 711 and the vertical portion of the vertical snap-fit plate 613. The bottom of the cantilever hook beam 711 is fixed to the isolating wall of the fixed seat 7, and there is space for movement in front of, behind, and on the left and right of the upper portion of the cantilever hook beam 711.

After leaving the factory and before use: the support frame 712 of the fixed seat 7 extends from the lower portion of the slidable seat 6 through the fixed seat extension slot 614; the upper wall face of the isolating wall 71 of the fixed seat 7 abuts against the bottom wall face of the partition plate 61; and the fixed seat 7 cannot move upward relative to the slidable seat 6. The cantilever hook beam 711 extends out from the first groove 611. Part of the first snap-fit protrusion 7111 snap-fits at the upper end of the vertical snap-fit plate 613, and the fixed seat 7 cannot move downward relative to the slidable seat 6. The amount of the part of the first snap-fit protrusion 7111 snap-fit at the upper end of the vertical snap-fit 613 is designed according to the needs. It has strong designability, good controllability, a wide design range and a high structural reliability.

When the device is implanted and used, the lower end face of the slidable seat 6 is pressed against the skin. The fixed seat 7 is pushed downward. The cantilever hook beam 711 tends to move downward with the fixed seat 7. The lower end face of the first snap-fit protrusion 7111 starts to squeeze the upper end face of the vertical snap-fit plate 613. Under the reaction force of the upper end face of the vertical snap-fit plate 613, the upper end of the cantilever hook beam 711 is deformed inward and upward relative to its bottom, and the first snap-fit protrusion 7111 is gradually away from the support of the upper end face of the vertical snap-fit plate 613. A downward thrust is further applied to the fixed seat 7. After deformation to a certain extent, the first snap-fit protrusion 7111 is no longer supported by the upper end face of the vertical snap-fit plate 613. The inside vertical face of the vertical snap-fit plate 613 pushes the first snap-fit protrusion 7111 inward. The downward movement of the fixed seat 7 relative to the slidable seat 6 is no longer hindered, and the implantable needle carries the implantable sensing electrode with the fixed seat 7 to implant it into the skin.

The lower portion of the partition plate 61 is a fixed seat accommodating cavity 62, which accommodates the bottom cavity of the fixed seat 7. Snap-fit fingers 621 of unequal lengths extend inward from the fixed seat accommodating cavity 62. The vertical direction of the snap-fit finger 621 does not extend to the bottom of the fixed seat accommodating cavity 62. The bottom of the fixed seat 7 is the transmitter accommodating cavity 74. The main body of the implantable biological transmitter 10 is snap-fit in the interior of the transmitter accommodating cavity 74. The transmitter accommodating cavity 74 is composed of several sections of arc-shaped cantilever snap-fit beam 741 of different arc lengths. Before implantation, the snap-fit finger 621 pushes the arc-shaped cantilever snap-fit beam 741 from the outside. The arc-shaped cantilever snap-fit beam 741 can engage the implantable biological transmitter 10 tightly. When the arc-shaped cantilever snap-fit beam 741 is moved down to a certain extent relative to the fixed seat accommodating cavity 62, the arc-shaped cantilever snap-fit beam 741 is not pushed by the snap-fit finger 621 on the outside, and can be deformed outward, losing the snap-fit with the implantable biological transmitter 10. After the double-sided adhesive 1014 on the lower end face of the implantable biological transmitter 10 adheres to the skin, the implantable biological transmitter 10 also adheres to the skin. The slidable seat 6 and the fixed seat 7 are withdrawn, and the needle withdrawal action is completed. The implantable biological transmitter will not be taken away.

In the present embodiment, the first snap-fit protrusion 7111 is partially snap-fit at the upper end of the vertical snap-fit plate 613. The lower straight plane of the first snap-fit protrusion 7111 is pressed on the upper straight plane of the vertical snap-fit plate 613; and 30%-90% of the extension length of the first snap-fit protrusion 7111 is snap-fit at the upper end of the vertical snap-fit plate 613.

The first snap-fit protrusion 7111 snap-fit at the upper end of the vertical snap-fit plate 613 relates to the issue of how much is pushed. We define it as the amount of interference. In the case where it can be pushed open, a small amount of interference requires a small trigger force, and a big amount of interference requires a big trigger force. An appropriate amount of interference is controlled, and a structure which meets the required trigger force value can be designed. If the amount of interference is too large, the vertical snap-fit plate 613 cannot push open the cantilever hook beam 711. If the amount of interference is too small, under mechanical disturbance or vibration, the vertical snap-fit plate 613 can break the restraint of the cantilever hook beam 711, and it cannot perform the function of locking in this state.

In the present embodiment, the support frame 712 is configured to be slidable along the snap-fit frame 612.

The outer side of the support frame 712 is provided with a first vertical snap-fit strip 7121, and the inner side of the snap-fit frame 612 is provided with a first vertical snap-fit slot 6121. The first vertical snap-fit strip 7121 is slidable along the first vertical snap-fit slot 6121. The length of the first vertical snap-fit strip 7121 is greater than the length of the first vertical snap-fit slot 6121, providing space for the sliding of the fixed seat 7 relative to the slidable seat 6. The upper portion of the first vertical snap-fit strip 7121 is used to mate with the main housing 3.

The snap-fit frame 612 is divided into four portions, respectively located on the circumference of the fixed seat extension slot 614. The corresponding support frame 712 is divided into four portions. A first vertical snap-fit slot 6121 is provided on the inner side of the snap-fit frame 612 of each portion. A first vertical snap-fit strip 7121 is provided on the outer side of the support frame 712 of each portion. Each first vertical snap-fit strip 7121 fits into a first vertical snap-fit slot 6121 correspondingly.

In the present embodiment, it further comprises a needle drive 4 and a compression spring 5.

An inner jaw 41 is provided on the inner side the needle drive 4 for snap-fit with the needle aid 11, and a snap-fit column 713 in the spring extends upwards from the isolating wall 71 on the inner side the support frame 712.

The support frame 712 further comprises a cantilever pressure contact beam 7122, which is provided on the upper end with a pressure contact 71221 facing inward.

The upper portion of the snap-fit frame 612 is provided with a section of pressure contact plate 6122.

After leaving the factory and before use: the lower end of the compression spring 5 abuts against the upper wall face of the isolating wall 71. The upper end of the compression spring 5 abuts against the inner bottom face of the needle drive 4.

The lower portion of the compression spring 5 is sleeved outside the snap-fit column 713 in the spring. The upper portion of the compression spring 5 is sleeved outside the inner jaw 41. The compression spring 5 is in a compressed state. The pressure contact 71221 is pressed against the bevel on the circumference of the needle drive 4. The pressure-contact face of the pressure contact 71221 is also a bevel. Pressed by the pressure contact plate 6122 on the outside, the cantilever pressure contact beam 7122 cannot be deformed outward, so the needle drive 4 cannot push open the cantilever pressure contact beam 7122 outward.

In use, after the fixed seat 7 moves down for a distance relative to the slidable seat 6, the needle aid 11 completes the implantation action. After the implantable sensing electrode is implanted into the subcutaneous tissue, the cantilever pressure contact beam 7122 is released from the pressure contact of the pressure contact plate 6122, and the pressure contact 71221 of the pressure contact plate 6122 is no longer pressed against the bevel on the circumference of the needle drive 4. The upper portion of the needle drive 4 is no longer restrained. Under the effect of the elastic potential energy of the compression spring 5, the needle drive 4 pushes open the pressure contact 71221. The inner jaw 41 of the needle drive 4 drives the needle aid 11 to move upward to complete the needle withdrawal.

The snap-fit frame 612 is divided into four portions. There are four pressure contact plates 6122. A pressure contact plate 6122 is provided between each pair of snap-fit frames 612. There are four cantilever pressure contact beams 7122. Each pressure contact plate 6122 corresponds to a cantilever pressure contact beam 7122.

The snap-fit column 713 inside the spring is distributed in an arc shape. There are four or more snap-fit columns 713 inside the spring. The snap-fit columns 713 inside the spring are distributed in a circumferential array to be stably supported on the inner side the compression spring 5.

In the present embodiment, it further comprises a main housing 3, which is provided with a second vertical snap-fit slot 31 and a snap-fit plate 32. The snap-fit plate 32 is provided with a snap-fit groove 325. A snap-fit block 7125 is provided on the outer side the support frame 712. The upper portion of the first vertical snap-fit strip 7121 is snapped into the second vertical snap-fit slot 31. The snap-fit block 7125 is fitted in the snap-fit groove 325, so that the main housing 3 and the fixed seat 7 are assembled and are fixed in relation to each other. The main housing 3 is located on the outer side the slidable seat 6 and the fixed seat 7.

It further comprises an upper cover 01. The upper cover 01 fits on the outer side of the main housing 3 through a snap-fit interface. The upper cover 01 fits on the upper portion of the main housing 3 through its lower snap-fit structure. The main housing 3 is open at the top before the upper cover 01 is assembled to facilitate manufacturing and assembly, in order to facilitate the assembly of the overall structure.

In the present embodiment, it further comprises a main device protective jacket 16. The lower circumference of the fixed seat 7 is for snap-fit with the implantable biological transmitter 10. The main device protective jacket 16 snap-fits with the lower portion of the main housing 3. The slidable seat 6 and the fixed seat 7 are located in the space formed by the main device protective jacket 16 and the main housing 3.

The implantable biological transmitter 10 includes a transmitter main body and an implantable sensing electrode 022. In an embodiment, the transmitter main body and the implantable sensing electrode 022 have been assembled.

In another embodiment, the implantable biological transmitter 10 in the first stage does not include the implantable sensing electrode 022. Instead, the assembly of the main body of the implantable biological transmitter 10 and the implantable sensing electrode 022 is completed in a preceding step before implantation. The implantable sensing electrode 022 is disposed in the main device protective jacket 16. An assembly space is reserved between the main housing 3 and the main device protective jacket 16. The main housing 3 and the main device protective sleeve 16 move relative to each other, realizing the assembly of the implantable sensing electrode 022 and the main body of the implantable biological transmitter 10.

In the present embodiment, it further comprises a needle aid 11, which comprises an implantable needle 111 and a needle seat 112. The needle seat 112 is provided at the upper end with a snap-fit groove for snap-fit with the inner jaw 41.

When it leaves the factory, the inner jaw 41 snap-fits with the snap-fit groove of the needle seat 112. Alternatively, snap-fit between the inner jaw 41 and the snap-fit groove of the needle seat 112 is achieved through the first step action after it leaves the factory and before implantation.

In the present embodiment, it further comprises an anti-trigger sleeve 14, which is snap-fit between the main housing 3 and the main device protective jacket 16. The main device protective jacket 16 is provided at the bottom with an assembly snap-fit seat 161. The assembly snap-fit seat 161 is used for snap-fit with the sensing electrode assembly 02. The sensing electrode assembly 02 comprises an electrode protective jacket 021, a needle aid 11, an implantable sensing electrode 022 and an electrode assembly main body 023. The electrode protective jacket 021 is provided with a soft plug 0211. The upper end of the electrode protective jacket 021 fits in the lower portion of the electrode assembly main body 023. The bottom of the electrode protective jacket 021 is plugged by the soft plug 0211. Disinfection and sterilization treatment is performed after plugging.

After leaving the factory and before use: the sensing electrode assembly 02 and the main body of the implantable biological transmitter 10 are configured separately. The implantable biological transmitter 10 fit at the lower circumference of the fixed seat 7 only comprises the main body and does not comprise the implantable sensing electrode 022. In the first stage before implantation, the anti-trigger sleeve 14 is removed first, so that the main housing 3 moves relative to the main device protective jacket 16. The main housing 3 drives the main body 101 of the implantable biological transmitter 10 close to the sensing electrode assembly 02 through the fixed seat 7, completing the fit between the main body 101 of the implantable biological transmitter 10 and the implantable sensing electrode 022. The main body 101 comprises a transmitter upper cover 1011, a transmitter PCBA 1012, a transmitter housing 1013 and a double-sided adhesive 1014. The transmitter upper cover 1011, transmitter PCBA 1012, transmitter housing 1013 and double-sided adhesive 1014 have been assembled before leaving the factory. The transmitter PCBA 1012 fits between the transmitter upper cover 1011 and the transmitter housing 1013, and the double-sided adhesive 1014 is bonded to the bottom of the transmitter housing 1013. The transmitter housing 1013 and the transmitter upper cover 1011 are provided with a structure for snap-fitting with the sensing electrode assembly 02. Snap-fit is completed as they approach each other. The circuit board of the transmitter housing 1013 or the transmitter PCBA 1012 is provided with a circuit breaker. The main body of the implantable biological transmitter 10 is in an open circuit state before fitting with the sensing electrode assembly 02. The sensing electrode assembly 02 is provided with a touch switch. After the main body 101 of the implantable biological transmitter 10 fits with the sensing electrode assembly 02, the touch screen switch enables the main body of the implantable biological transmitter 10 to communicate with the sensing electrode assembly 02 to be in a conducting state.

In an embodiment, the sensing electrode assembly 02 is provided in the upper portion with a spring pin. The circuit board of the transmitter housing 1013 or transmitter PCBA 1012 is provided with a round hole. Both sides of the round hole are in a non-conducting state. After the spring pin is inserted into the round hole, both sides of the round hole are in a conducting state.

The above is only a preferred embodiment of the invention. It should be pointed out that for those skilled in the art, several improvements can be made without departing from the principle of the invention. These improvements should also be considered as the protection scope of the invention.

The invention claimed is:

1. An implantable device for an implantable biological transmitter (10), comprising: a slidable seat (6) and a fixed seat (7); wherein, the slidable seat having a partition plate (61) separating the slidable seat into a fixed seat accommodating cavity (62) and an upper portion, with a fixed seat extension slot (614) and at least two first grooves (611) penetrating the slidable seat having the partition plate (61), and the slidable seat further comprising a vertical snap-fit plate (613) extending from the partition plate (61) into the upper portion and disposed on an outer side of the first grooves;

the fixed seat (7) is slidably engaged with the slidable seat (6), the fixed seat (7) comprising: an isolating wall (71) received in the fixed seat accommodating cavity (62) and configured to snap-fit with the implantable biological transmitter (10) at a lower circumference thereof away from the partition plate (61); at least two cantilever hook beams (711) extending from the isolating wall (71) and each of the cantilever hook beams (711) extending through a respective one of the first grooves (611), each of the cantilever hook beams having a first snap-fit protrusion (7111) at an upper end of the cantilever hook beam away from the isolating wall (71); and a support frame (712) extends from the isolating wall (71) through the fixed seat extension slot (614) and slidably engaged with the slidable seat (6);

the implantable device further comprises a needle drive (4) received in the support frame (712) and a compression spring (5) disposed between the isolating wall (71) and the needle drive (4), the needle drive (4) comprising an inner jaw (41) for snap-fit with a needle aid (11) associated with the implantable biological transmitter (10), the fixed seat (7) further comprises a snap-fit column (713) extending from the isolating wall (71) on an inner side of the support frame (712) and disposed in the compression spring (5);

wherein, in a pre-use state:

the fixed seat (7) is locked relative to the slidable seat (6) by (i) the isolating wall (71) abutting against the partition plate (61), and (ii) each first snap-fit protrusion (7111) snap-fitting with an upper end of a corresponding snap-fit plate (613); and wherein, in a triggered state:

a downward force is transmitted to the fixed seat (7), causing the first snap-fit protrusions (7111) to disengage from the snap-fit plates (613) and driving the fixed seat (7) to slide towards the implantable biological transmitter (10), thereby driving the implantable biological transmitter (10) to implant into a user's tissue; and the fixed seat (7) moves until the needle drive (4) gets released from the snap-fit with the needle aid (11) of the implantable biological transmitter (10), allowing the compression spring (5) to expand and drive the needle drive (4) to retract.

2. The implantable device of claim 1, wherein each first snap-fit protrusion (7111) and the corresponding snap-fit plate (613) is snap-fit in such a way that a lower straight plane of the first snap-fit protrusion (7111) facing the isolating wall (71) is pressed on an upper straight plane of the snap-fit plate (613) opposite to the partition plate (61), and wherein 30% to 90% of the first snap-fit protrusion in an extension length direction is in snap-fit engagement with the snap-fit plate (613).

3. The implantable device of claim 1, wherein the support frame (712) comprises a first snap-fit strip (7121) on an outer side of the support frame away from the needle drive (4), the slidable seat (6) comprises a snap-fit frame (612) having a first snap-fit slot (6121) on an inner side of the snap-fit frame adjacent to the support frame (712), and the first snap-fit strip (7121) is slidably received within the first snap-fit slot (6121).

4. The implantable device of claim 3, wherein the implantable device further comprising a main housing (3) for receiving the slidable seat (6) and the fixed seat (7), with a second snap-fit slot (31) and a snap-fit plate (32) formed inside the main housing (3), the snap-fit plate (32) having a snap-fit groove (325), wherein the support frame (712) comprises a snap-fit block (7125) on the outer side of the support frame away from the needle drive (4), and wherein an upper portion of the first snap-fit strip (7121) is engaged with the second snap-fit slot (31) and the snap-fit block (7125) is engaged within the snap-fit groove (325).

5. The implantable device of claim 4, wherein the support frame (712) further comprises a cantilever pressure contact beam (7122) between the snap-fit frame (612) and the needle drive (4), the cantilever pressure contact beam (7122) having an inward-facing pressure contact (71221) at an upper end away from the isolating wall (71); and the snap-fit frame (612) is further provided with a pressure contact plate (6122) extending inward to the cantilever pressure contact beam (7122);

wherein, in the pre-use state, the pressure contact plate (6122) restrains an outward deformation of the cantilever pressure contact beam (7122), and the pressure contact (71221) engages a beveled surface on the needle drive (4).

6. The implantable device of claim 5, further comprising a main device protective jacket (16) snap-fitting with an end of the main housing (3) to form a space, and the slidable seat (6) and the fixed seat (7) are located in the space.

7. The implantable device of claim 6, further comprising an anti-trigger sleeve (14) removably snap-fit between the main housing (3) and the main device protective jacket (16) to prevent a relative movement therebetween the main housing (3) and the main device protective jacket (16) in the pre-use state.

8. The implantable device of claim 7, wherein:

the main device protective jacket (16) comprises an assembly snap-fit seat (161) at a bottom of the main device protective jacket away from the main housing (3), configured to releasably hold a sensing electrode assembly (02) comprising an implantable sensing electrode (022).

9. The implantable device of claim 8, wherein the needle aid (11) comprises a needle seat (112) having a snap-fit groove, and the inner jaw (41) snap-fits into the snap-fit groove.

\*   \*   \*   \*   \*